(12) United States Patent
Sullivan et al.

(10) Patent No.: US 9,089,685 B2
(45) Date of Patent: Jul. 28, 2015

(54) WEARABLE DEFIBRILLATOR WITH A MULTIVECTOR SHOCK WAVEFORM

(71) Applicant: WEST AFFUM HOLDINGS CORP., Grand Cayman (KY)

(72) Inventors: Joseph L. Sullivan, Redmond, WA (US); Isabelle Banville, Redmond, WA (US); Richard C. Nova, Redmond, WA (US)

(73) Assignee: WEST AFFUM HOLDINGS CORP., Grand Cayman (KY)

(*) Notice: Subject to any disclaimer, the term of this patent is extended or adjusted under 35 U.S.C. 154(b) by 0 days.

(21) Appl. No.: 14/189,789

(22) Filed: Feb. 25, 2014

(65) Prior Publication Data

US 2014/0243918 A1   Aug. 28, 2014

Related U.S. Application Data

(60) Provisional application No. 61/769,098, filed on Feb. 25, 2013.

(51) Int. Cl.
*A61N 1/39* (2006.01)
*A61N 1/04* (2006.01)

(52) U.S. Cl.
CPC .............. *A61N 1/046* (2013.01); *A61N 1/0484* (2013.01); *A61N 1/39* (2013.01); *A61N 1/3918* (2013.01)

(58) Field of Classification Search
None
See application file for complete search history.

(56) References Cited

U.S. PATENT DOCUMENTS

| 6,065,154 | A | 5/2000 | Hulings et al. | |
|---|---|---|---|---|
| 6,334,070 | B1 | 12/2001 | Nova et al. | |
| 6,356,785 | B1 | 3/2002 | Snyder et al. | |
| 7,865,238 | B2 * | 1/2011 | Brink | 607/7 |
| 2005/0107833 | A1 | 5/2005 | Freeman et al. | |
| 2005/0107834 | A1 | 5/2005 | Freeman et al. | |
| 2012/0158075 | A1 | 6/2012 | Kaib et al. | |
| 2012/0265265 | A1 * | 10/2012 | Razavi et al. | 607/7 |
| 2014/0163663 | A1 | 6/2014 | Poddar et al. | |

* cited by examiner

*Primary Examiner* — Brian T Gedeon
(74) *Attorney, Agent, or Firm* — Baker & Hostetler LLP (57) ABSTRACT

A transthoracic defibrillator for external defibrillation comprises at least three electrodes configured to be attached to the thorax of a patient to establish at least two electrical paths across the thoracic cavity and through the heart of the patient. In addition, a defibrillator circuit contained in a defibrillator housing has the capability to deliver a different defibrillation waveform across each of the at least two electrical paths.

18 Claims, 7 Drawing Sheets

<u>MAIN TYPES OF EXTERNAL DEFIBRILLATORS</u>

| Type of defibrillator | How applied | Rhythm Interpretation | Therapy delivery |
|---|---|---|---|
| Defib – Monitor | Medical professionals | Manually by medical professionals | Manually by medical professionals |
| AED | Applied by lay people | Automatically by device | Automatically or semi-automatically |
| Wearable | Worn by patient | Automatically by device | Automatically by device |

WEARABLE DEFIBRILLATOR WITH A MULTIVECTOR SHOCK WAVEFORM

CROSS REFERENCE TO RELATED APPLICATIONS

This application claims the benefit of U.S. Provisional Application No. 61/769,098, filed Feb. 25, 2013, which is hereby incorporated by reference in its entirety.

TECHNICAL FIELD

The present invention relates generally to external defibrillators, and more particularly to a multivector shock protocol for use by an external, wearable defibrillator.

BACKGROUND

Figure 1:
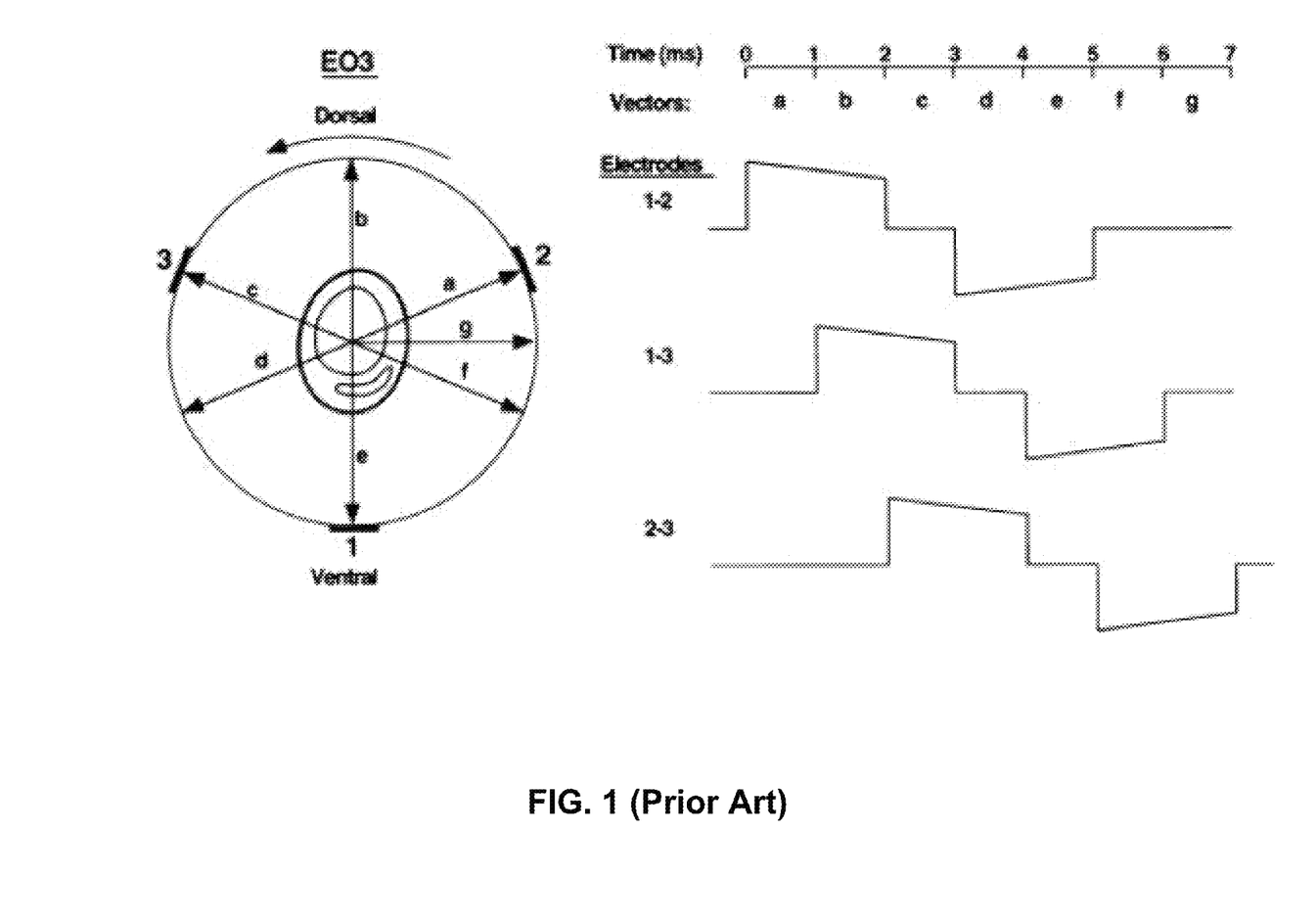
FIG. 1 depicts the electrode positions used in the Pagan-Carlo study and the timing of the associated waveforms.

The energy delivered by a defibrillator is typically expressed in Joules. Energy has become a surrogate for current in modern defibrillator language, but electrical current is what actually defibrillates the heart. A Joule is the unit of work associated with one amp of current passed through one ohm of resistance for one second. Electrical current may be expressed as the ratio of voltage/impedance. Both the patient and the electrical circuit of the defibrillator contain impedance, which is expressed in ohms A multivector shock is one which utilizes three or more therapy electrodes to deliver electrical current along at least two separate current paths. Studies have shown that multivector shocks can substantially reduce the energy required for defibrillation. For example, Pagan-Carlo et al. (JACC 1998) demonstrated that a multivector shock can defibrillate pigs with about 40% less energy than a standard biphasic truncated exponential (BTE) waveform. FIG. 1 is an illustration of the electrode positions used in this study and the timing of the associated waveforms. The authors used three electrodes to generate a series of 7 different shock vectors. According to this method, current is initially delivered from electrode 1 to electrode 2. This continues for 1 ms, then current is delivered from electrode 1 to electrodes 2 and 3 together. This continues for another millisecond. Then current is delivered from electrodes 1 and 2 to electrode 3. The shock sequence continues to switch between electrode combinations (i.e. "vectors") until all seven vectors have been energized.

Figure 2:
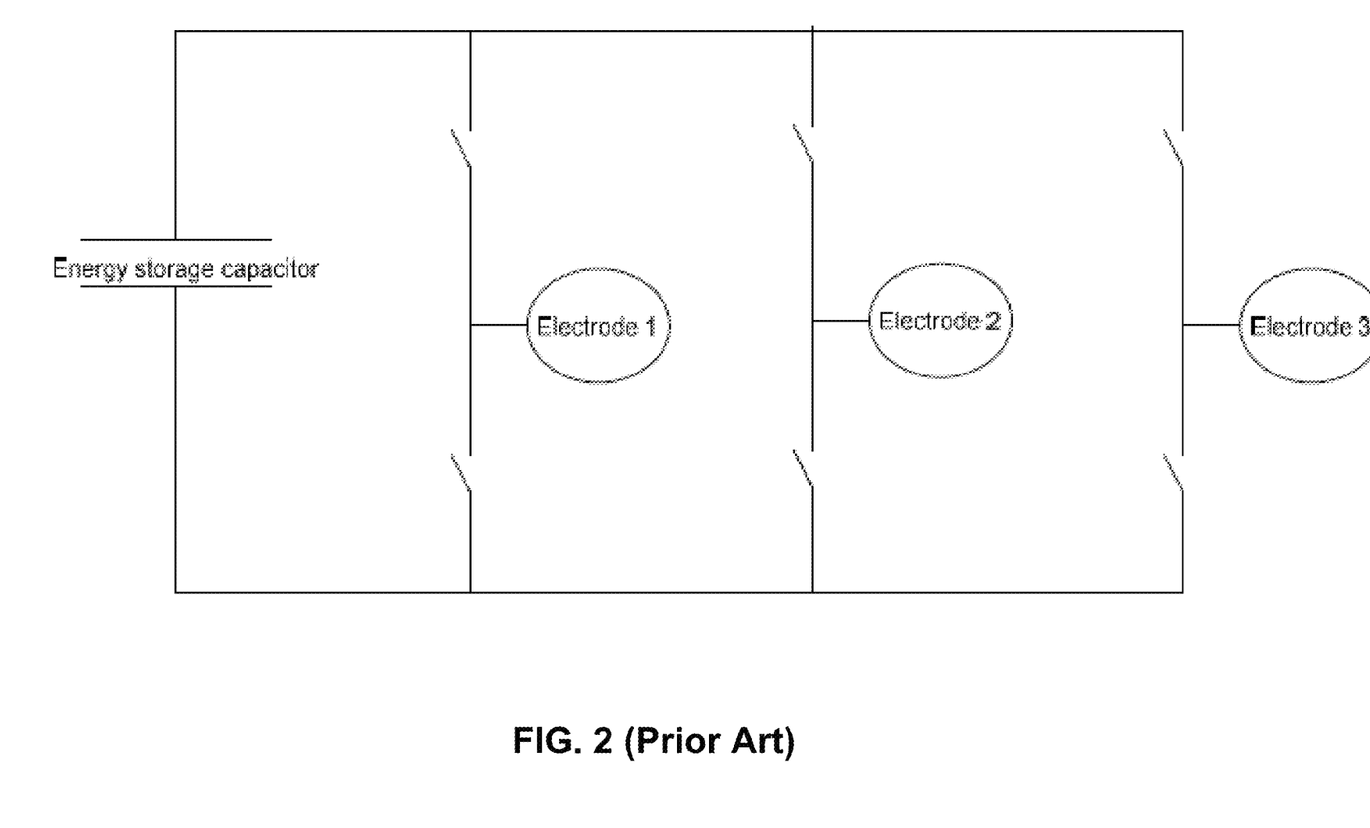
FIG. 2 depicts circuit for delivering a three-electrode multivector shock.

A circuit for delivering a three electrode multivector shock is shown in FIG. 2. Note that this implementation delivers a multivector shock from a single capacitor. In this respect, it is different from the configuration disclosed by published patent application US 2005/0107834, entitled "Multi-path Transthoracic Defibrillation and Cardioversion". As shown, the circuit of FIG. 2 contains three half-bridges, one for each electrode. If more electrodes were utilized, more half-bridges would be required. Each of the switches could be a semiconductor switch such as an IGBT (insulated-gate bipolar transistor), SCR (silicon-controlled rectifier), MOSFET (metal-oxide-semiconductor field-effect transistor), BiMOSFET (bipolar MOSFET), or similar device. The switches in the FIG. 2 circuit are operated sequentially to deliver current to different combinations of electrodes as described above.

While Pagan-Carlo achieved good results with their shock sequence of 7 vectors, it is not clear whether that particular sequence is optimal or necessary. A smaller number of shock vectors may be equally efficacious as well as being easier to implement. For example, two shock vectors (electrode 1→electrode 2, followed by electrode 1→electrode 3) may be appropriate. In other words, a shock sequence with two or more vectors may be superior to a standard single-vector shock.

Historically, in defibrillator applications, multivector waveforms have been unattractive because of the difficulty of properly applying three or more electrodes to a patient. When a rescuer is treating a cardiac arrest patient, time is of the essence. The extra time required to apply extra defibrillation pads could be critical for survival. Applying a back pad is particularly difficult to do to a patient that is unconscious. Also, training rescuers to apply pads in novel, new locations would be difficult and confusing.

Many of the obstacles that complicate the application of a multivector shock can be overcome by a carefully designed wearable defibrillator. A wearable defibrillator may include a garment (such as a vest), a belt, or other arrangement that provides access to multiple points on the patient's thorax. This garment may allow multiple therapy electrodes to be easily placed in advantageous locations without extra hassle or confusion. Because the patient is conscious it is not difficult to access the patient's back.

A multivector defibrillator may be particularly advantageous for a wearable defibrillator because it may allow the use of smaller therapy electrodes. Pagan-Carlo proposed an "overlapping encircling" shock scheme that uses the available electrodes in different combinations to create a rotating shock vector that sweeps around the heart. This scheme uses electrodes in pairs and threesomes to create seven different shock vectors.

For a conventional two-electrode (single vector) defibrillation shock the size of the pads plays a role in ensuring the proper current distribution through the heart. In order for the shock to be successful, enough of the heart must receive enough current to depolarize the heart cells. Pads that are too small may not deliver enough current to some parts of the heart. In contrast to a conventional defibrillator, a multivector defibrillator may be able to use smaller pads because current flow through all parts of the heart is guaranteed by the multivector waveform not by pad size alone.

Therapy electrodes for multivector defibrillation might be applied to the patient in different arrangements. Pagan-Carlo suggested that the three pads be equally distributed around the perimeter of the thorax. This could be implemented using two anterior pads, one approximately beneath each breast, and one posterior pad in the middle of the back. Alternatively, there could be one anterior pad over the sternum and two back pads. Although Pagan-Carlo's arrangement worked well for pigs it is unclear whether it would be ideal for humans. The cross-section of a pig's thorax is much more cylindrical than a human's thorax and electrodes placed laterally on a human could deliver current relatively far from the heart.

SUMMARY

A goal of the present invention is to leverage such an energy reduction to design a small and lightweight defibrillator, e.g., a wearable defibrillator (although the invention is by no means limited to a wearable device). As described below, two aspects of the present invention concern placement of the electrodes to avoid current through the patient's lungs, and controlling the total tilt of the multivector waveform.

In wearable defibrillators, the energy storage capacitor can be the single largest component of the defibrillator. The energy storage capacitor and energy delivery circuit do not lend themselves to miniaturization like other electronic components do. These components can be reduced in size, however, by reducing the energy of the electrical waveforms delivered to the patient. The present disclosure provides one way of reducing the energy. For example, the present invention could enable construction of a 90 Joule wearable defibrillator that has the same shock success rate as a 150 Joule wearable defibrillator. This would allow the inventive wearable defibrillator to be smaller and lighter weight, providing a significant customer advantage.

In a first embodiment of the present invention, a transthoracic defibrillator for external defibrillation comprises at least three electrodes configured to be attached to the thorax of a patient to establish at least two electrical paths across the thoracic cavity and through the heart of the patient. In addition, a defibrillator circuit contained in a defibrillator housing is operatively connected to the at least three electrodes and has the capability to deliver a different defibrillation waveform across each of the at least two electrical paths.

Another aspect of the present invention provides a method of transthoracic defibrillation. An illustrative embodiment of the inventive method comprises the step of attaching at least two electrodes to the thorax of a patient to establish at least a first electrical path across the thoracic cavity and through the heart of the patient. In addition, in this embodiment, the method includes determining if the patient is in ventricular tachycardia (VT), ventricular fibrillation (VF), or atrial fibrillation (AF), and establishing at least a second electrical path if VF or AF is determined The step of establishing at least a second electrical patent comprises attaching at least one additional electrode to the thorax of the patient to establish at least one additional electrical path across the thoracic cavity and through the heart of the patient. Finally, a defined amount of electrical energy is delivered as a first shock across at least one of the electrical paths.

Other features of the present invention are described below.

DETAILED DESCRIPTION OF ILLUSTRATIVE EMBODIMENTS

As mentioned, an illustrative embodiment of the present invention is suitable for use as a wearable defibrillator for human patients. One example of a multivector arrangement for humans would be a four electrode configuration with two pads in standard apex-sternum positions along with two electrodes in standard anterior-posterior position. (Readers skilled in the art of defibrillators are assumed to know the standard positions for electrodes.) This would allow for two orthogonal current paths both of which would be along vectors that are known to be effective.

In the following detailed description, we describe illustrative examples of electrode placement and waveform control protocols in accordance with the present invention. We also describe example embodiments of external defibrillator hardware structures in accordance with the present invention.

Electrode Placement to Avoid Current Through the Lungs

Multiple electrodes could be placed on a single pad substrate for easier application and positioning and cable management. One of the problems with a standard apex-sternum pad placement is that current flow must go through the lungs. Lungs are relatively high impedance so they tend to restrict current flow. Electrodes placed centrally on the chest and back can create current paths that avoid the lungs and may deliver a higher fraction of the current to the heart. A multi-vector electrode arrangement that attempts to avoid current paths through the lungs could have two anterior pads, both placed along the center line of the chest, and one or more back pads. Alternatively, it could have two back pads with both placed near the spine and a single chest electrode. In either of these arrangements a multivector shock sequence could be generated by delivering current sequentially along different current paths that are generated by connecting the energy to electrodes in different combinations.

We have tested some multivector waveforms in an animal lab setting. This study compared single vector biphasic shocks with multivector biphasic shocks. The multivector shocks were delivered with four electrodes, with electrodes A and B placed in an anterior-posterior position, and electrodes C and D placed in lateral-lateral position. A number of shock waveforms were tested, but the most interesting are illustrated in FIG. 3A.

Figure 3A:
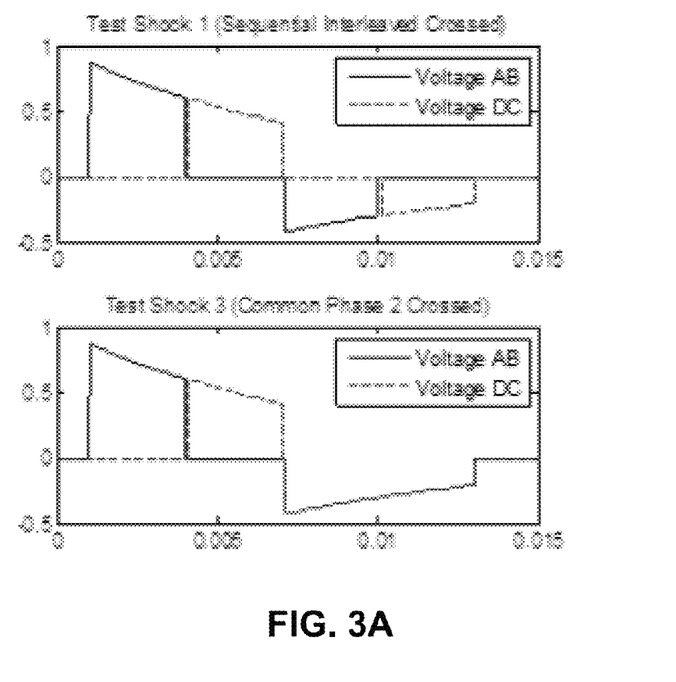
FIG. 3A depicts a number of interesting shock waveforms tested for use with illustrative embodiments of the present invention.

In FIG. 3A, Test shock 1 has four sub-pulses: a 3 ms positive pulse along vector A-B, a 3 ms positive pulse along D-C, a negative 3 ms A-B pulse, and a negative 3 ms C-D pulse. For Test shock 3 the first two sub-pulses are the same as Test shock 1, but the negative pulse is 6 ms and is given along vectors A-B and C-D simultaneously. Both of these waveforms defibrillated with about 40% less energy than a conventional single-vector BTE shock. Such a shock waveform could allow a 90 J multivector defibrillator to have the same shock success rate as a 150 J single-vector defibrillator.

Figure 3B:
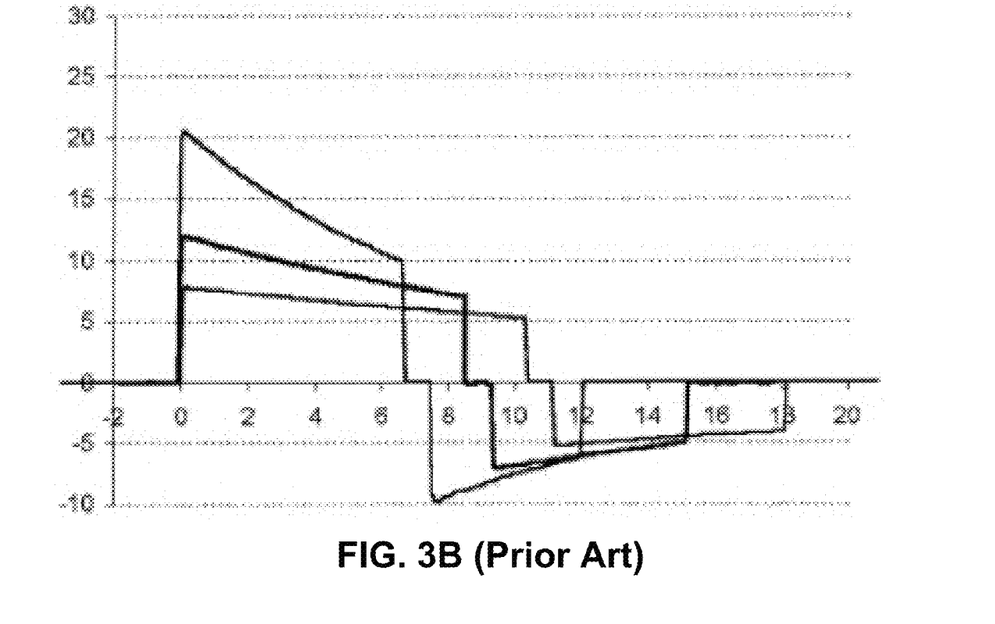
FIG. 3B depicts how a prior-art defibrillator adjusts the shock waveform for impedances of 50, 100, and 150 ohms

These shock waveforms are intended for a defibrillator that uses a single capacitor and uses a waveform that is time-multiplexed between vectors. A multivector waveform may adjust the pulse width to accommodate patients with different impedances. FIG. 3B is an illustration of how a prior-art defibrillator adjusts the shock waveform for different impedances (50, 100, and 150 ohms). A multivector defibrillator may use a scheme in which each phase is divided between two or more vectors. The waveforms shown in FIG. 4 all represent single capacitor waveforms. Because all of the energy is drawn from one capacitor, the starting voltage of one pulse will equal the trailing edge voltage of the preceding pulse. However, the current may be different along the two vectors because the impedance may differ.

Controlling the Waveform Total Tilt

One method of controlling the shock waveform is to specify the total tilt of the waveform (from the leading edge of the first pulse to the trailing edge of the last pulse) and give four equal duration sub-pulses. In order to do this, the resistance of each shock vector should be known. The formula for the duration of the sub-pulses is:

$$t = -R1*R2*C*\ln(\text{tilt})/2(R1+R2)$$

where,

R1=the resistance along one vector

R2=the resistance along the other vector

C=the capacitance of the energy storage capacitor tilt=the total tilt of the shock waveform t=the duration of each sub-pulse.

Although the present disclosure is suitable for a wearable defibrillator, a multivector waveform could be useful for non-wearable defibrillators as well. There are some situations in which the shock efficacy of existing biphasic defibrillators is inadequate and patients may benefit from a multivector waveform. There are also situations in which the drawback of needing to apply multiple electrodes may not be significant.

Cardioversion of atrial fibrillation. This is an elective procedure, so there is plenty of time to apply multiple defibrillation pads. Clinicians want to cardiovert atrial fibrillation with as little energy as possible, but there are some patients for whom 360 J is inadequate. A multivector shock waveform may be able to convert most patients with less energy. Some of the patients that cannot be converted with a single vector 360 J shock may be converted with a multivector 360 J shock.

Electrophysiology lab procedures. Again, this is an elective procedure. While defibrillation success rates are generally very in this setting, clinicians have strong desire to have the most effective therapy possible because they do not want their patient to die during their procedure.

Pre-hospital shocks for hard-to-defibrillate patients. Clinicians sometimes deliver simultaneous shocks with two defibrillators if a single 360 J shock doesn't work. A 360 J multivector would have a much higher efficacy than a single-vector shock, possibly eliminating the need to expose the patient to 720 J of energy.

Logic for Which Pads to Apply

There are several options for deciding which electrode pads to use for a given patient. For example, instructions could be provided to the user to apply one set of pads for ventricular tachycardia (VT), which is generally easy to convert, but multiple pads for ventricular fibrillation (VF) or atrial fibrillation (AF). This could be included in the instruction manual, or if the device detects the rhythm type, the device could prompt the user to apply the appropriate pads.

Alternatively, one set of pads could be initially applied to cardiac arrest patients to allow treatment to begin quickly. If shocks are not effective, then a second set of pads could be applied.

Another option is to place two pads in anterior-posterior position and two pads in anterior-lateral position to form orthogonal vectors. The two vectors are intended to be orthogonal and the pads should be placed as far apart as possible.

Logic for Which Pads to Excite

Similarly, there are several options for deciding which electrode pads to excite in a given situation. For example, the defibrillator could detect which pads were applied to the patient and apply energy accordingly. If two pads were applied, then energy would be delivered through those pads alone. If four pads were applied then a multivector shock would be applied. A single vector shock could be delivered through pairs of pads thereby increasing the effective surface area for delivery. Of the four pads the defibrillator accepts, any two pads could be applied to form a single shock vector. In other words, it is not necessary for the pads to come in predefined pairs that must be used together. This reduces the likelihood of a person making a mistake by applying only two pads that are not compatible.

Another option is to permit the user to select which pads form which vector. If pads A, B, C, and D are applied to the patient, the operator could tell the device that A-B form the anterior-posterior vector, and C-D form the lateral-lateral vector.

For a wearable defibrillator, the prescribing physician could decide whether a given patient should receive a single-vector shock or multivector shock. For a single-vector shock, he or she could also decide if it is to be an anterior-posterior vector or a lateral-lateral vector. Patients who are hard to defibrillate may require a multivector shock. A patient who is easy to defibrillate may be able to use a single vector shock. If the device is configured for a single vector, then the patient could wear a garment that only includes two pads, making the garment more comfortable.

Premeasure Impedance with Carrier Frequency

Before applying a defibrillation shock to a pair of electrodes it is necessary to verify that the pads are properly attached to the patient. This is often done with a carrier frequency. However, if two carrier frequency signals are injected into a single patient they could interfere with each other. There are several ways to solve this problem:

a. Measure impedance between pads A and B with frequency 1, and simultaneously measure impedance between pads C and D using a different frequency 2. Frequencies 1 and 2 can differ by significant amounts, for example 60 kHz and 65 kHz.

b. Alternate impedance measurements. Measure impedance A-B first, then C-D.

c. For a wearable defibrillator, measure impedance at a different time, possibly several times each day, but not when the patient is in cardiac arrest.

d. Continuously monitor wearable device impedance on each vector.

e. Check impedance between each pair of pads (six combinations) to detect if the pads have been misapplied. For example, if pads A and B are supposed to be on opposite sides of the body and C and D are supposed to be on opposite sides, then the A-B impedance should be higher than A-C or A-D. Adjust waveform/vector delivery accordingly to the appropriate path based upon detected impedance.

Waveform Control

Figure 4:
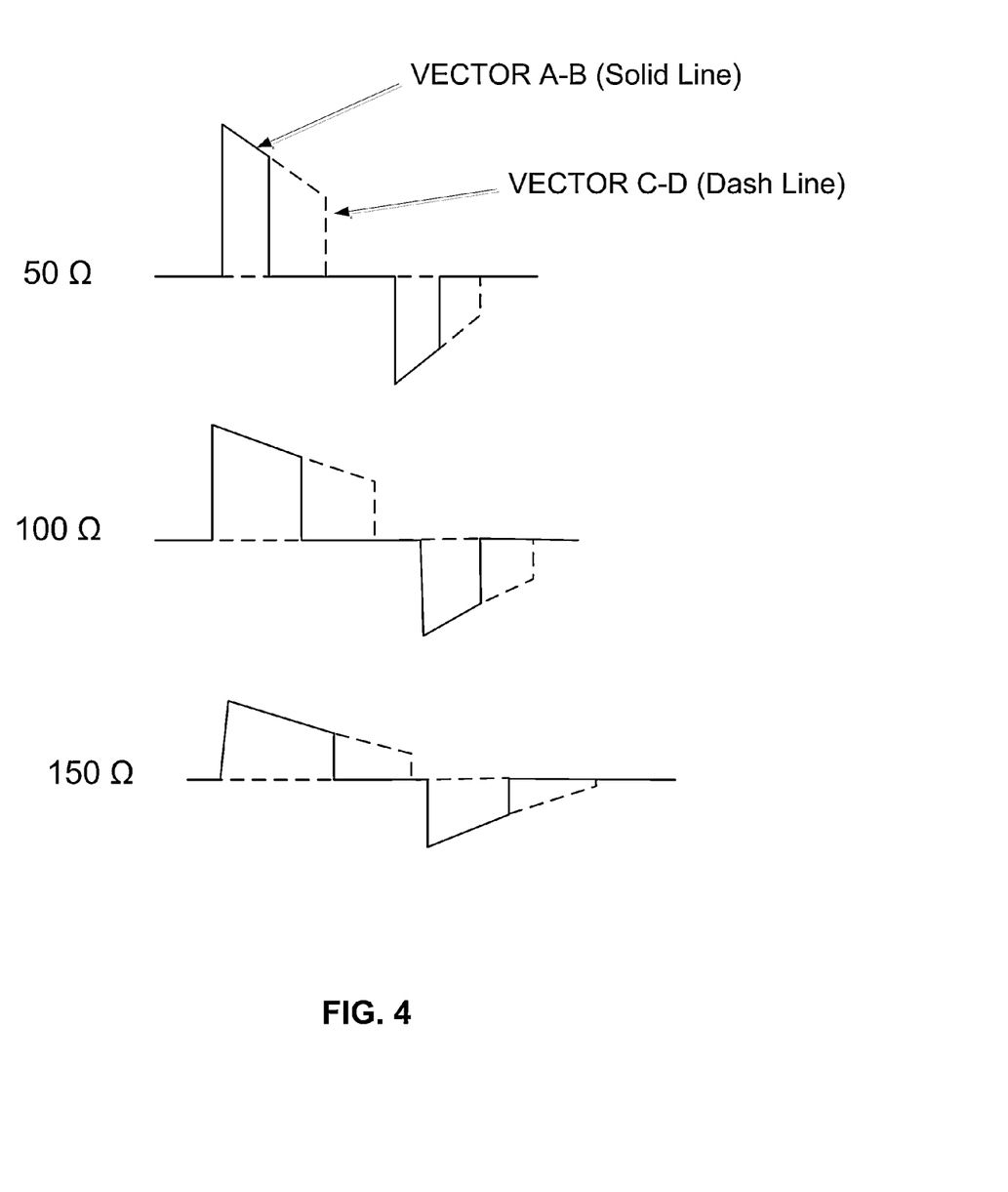
FIG. 4 depicts multivector waveforms for impedances of 50, 100, and 150 ohms These are similar to the waveforms of FIG. 3B but with each phase divided between two or more vectors.

The waveform control may be carried out in a number of ways. Parameters of the waveform that may be controlled include, but are not limited to, energy delivered, duration of a sub-pulse, duration of the entire waveform, and the waveform tilt. (The waveform "tilt" is defined as the ratio of (initial shock current–final shock current)/(initial shock current). Thus, a rectangular pulse has 0% tilt, one that decays to zero has 100% tilt, and most defibrillator waveforms are somewhere in the middle.) Any one of the following examples may be suited to a given situation:

a. Control each phase independently to deliver a specific amount of energy, or a specific tilt.

b. Shocks with interleaved phase 1 and interleaved phase 2 (Test shock 1 above) or interleaved phase 1 and common phase 2 (Test shock 3 above). The interleaved phases in FIG. 4 are shown as being the same duration, but they could also be different.

c. Configure the system to use a single capacitor to deliver the same amount of energy along each vector, for example 50 J on vector A-B, and 50 J on vector C-D. The capacitor voltage could be monitored until a predetermined amount of energy was delivered along one vector, then switch to the other vector. The duration of the two vectors may be different but the amount of energy they deliver is the same.

d. Deliver a time-multiplexed two-vector single capacitor shock through four electrodes in a manner such that the total duration increases with increasing impedance to give a specific amount of tilt. The impedance would be pre-measured along both vectors. The duration of each vector sub-pulse could be a fixed fraction of the total. The control of each sub-pulse is not independent—they vary together as impedance varies.

e. Deliver a single vector shock through two of the four electrodes based on the lowest impedance vector.

ECG Monitoring Through Therapy Pads

With four pads on the patient it is possible to use two pads to monitor and a third as a reference (right-leg drive). It is also possible to switch between multiple monitoring vectors, similar to the manner in which 3 lead ECG monitors switch between vectors. If enough pads are applied, it may be possible to construct a multi-lead ECG signal similar to a 12-lead ECG.

Fault Detection

If four pads are applied to the patient and a circuit fault is detected in one portion of the energy delivery circuit, it may be possible to compensate for the failure by only delivering energy through the portion of the circuit that is functional. For example, four half-bridge circuits are required to deliver energy to four electrodes. If one half bridge was broken, then the device could deliver a single vector shock through two half bridges, or a multivector shock through three half bridges. Fault detection could be performed during a device daily self-test, or it could be done in real-time during the shock (e.g. if a short circuit is suddenly detected).

If four electrodes are applied to the patient it is possible to use one set of pads as a backup in case there is a problem with the other pads. The switch to the backup could be done if one vector is insufficient to defibrillate or could be done if a fault is detected with one path.

External Defibrillator Embodiments

A wearable defibrillator system made according to embodiments has a number of components. One of these components is a support structure, which is configured to be worn by the patient. The support structure can be any structure suitable for wearing, such as a harness, a vest, one or more belts, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around at least the torso. Other embodiments could use an adhesive structure or another way for attaching to the person, without encircling any part of the body. There can be other examples.

Figure 5A:
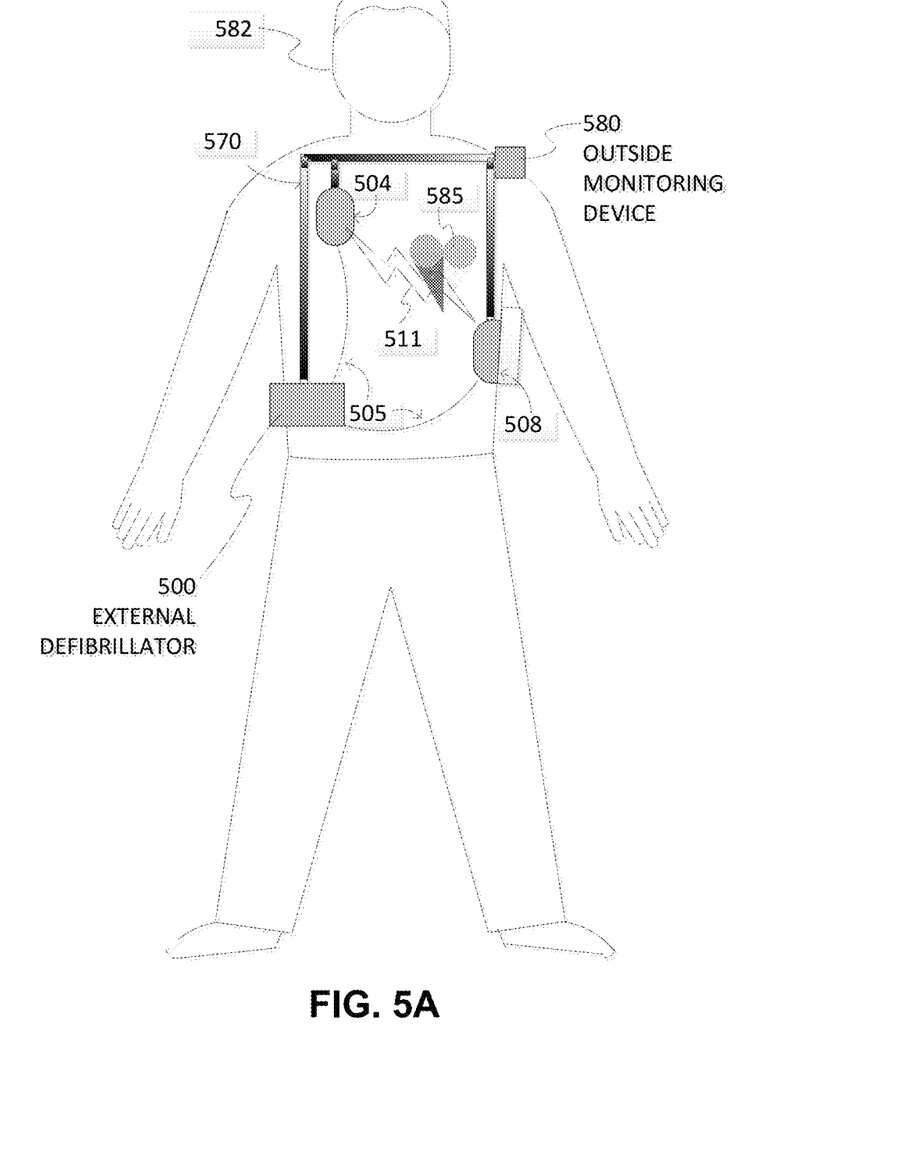
FIGS. 5A and 5B depict examples of an external, wearable defibrillation system.
Figure 5B:
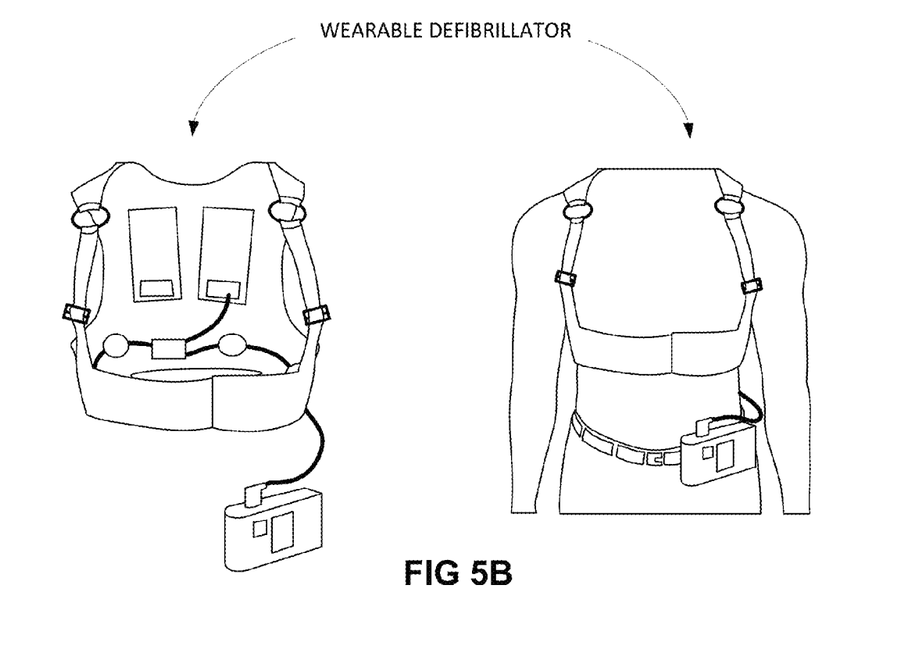

FIGS. 5A and 5B depict examples of a defibrillation system. FIG. 5A is a schematic rendering and FIG. 5B depicts an illustrative example of a wearable defibrillator. The left side of FIG. 5B shows the system itself and the right side shows the system being worn by a patient. As shown, with a wearable defibrillator, the patient wears the garment, which holds the electrodes in place and also has a manner of wearing or carrying the defibrillator with them. A multivector waveform is particularly suitable for a wearable defibrillator because the person can put on a single garment that includes multiple electrodes.

Referring to FIG. 5A, a person 582 is lying on his back. Person 582 could be a patient in a hospital, or someone found unconscious, and then turned to be on their back. Person 582 is experiencing a condition in his heart 585, which could be, e.g., ventricular fibrillation or the like. A portable external defibrillator 500 has been brought close to person 582. At least two defibrillation electrodes 504, 508 are usually provided with external defibrillator 500, and are sometimes called electrodes 504, 508. Electrodes 504, 508 are coupled with external defibrillator 500 via respective electrode leads 505. A rescuer (not shown) has attached electrodes 504, 508 to the skin of person 582. Defibrillator 500 is administering, via electrodes 504, 508, a brief, strong electric pulse 511 through the body of person 582. Pulse 511, also known as a defibrillation shock, goes also through heart 585, in an attempt to restart it, for saving the life of person 582. It should be noted that, in accordance with a presently preferred embodiment, the external defibrillator of FIG. 5A may include three or more electrodes strategically placed in a wearable garment to enable the application of a multivector shock protocol in accordance with the teachings of the present application. For example, a suitable configuration for humans would be a four electrode configuration with two pads in standard apex-sternum positions along with two electrodes in standard anterior-posterior positions.

Defibrillator 500 can be one of different types, each with different sets of features and capabilities. The set of capabilities of defibrillator 500 is determined by planning who would use it, and what training they would be likely to have.

Figure 6:
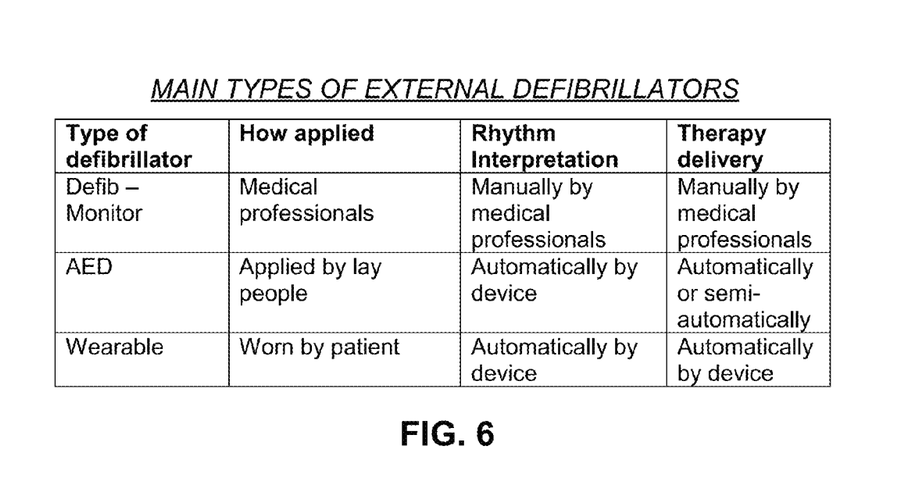
FIG. 6 depicts a table summarizing three main types of external defibrillators.

FIG. 6 depicts a table listing three main types of external defibrillators, how they are applied, interpreted, and configured for therapy delivery. A first type of defibrillator 500 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor can be used in a pre-hospital or hospital scenario. As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock. As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 500 is generally called an AED, which stands for "Automated External Defibrillator". An AED typically makes the shock/no shock determination by itself, automatically. Indeed, it can sense enough physiological conditions of the person 582 via only the shown defibrillation electrodes 504, 508. In some embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on. AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them. AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

A third type of defibrillator is a wearable defibrillator. It is prescribed by a physician, is worn by the patient, and applies therapy automatically in case of cardiac arrest.

There are additional types of external defibrillators, which are not listed in FIG. 6. For example, a hybrid defibrillator can have aspects of an AED, and also of a defibrillator-monitor. A usual such aspect is additional ECG monitoring capability.

Figure 7:
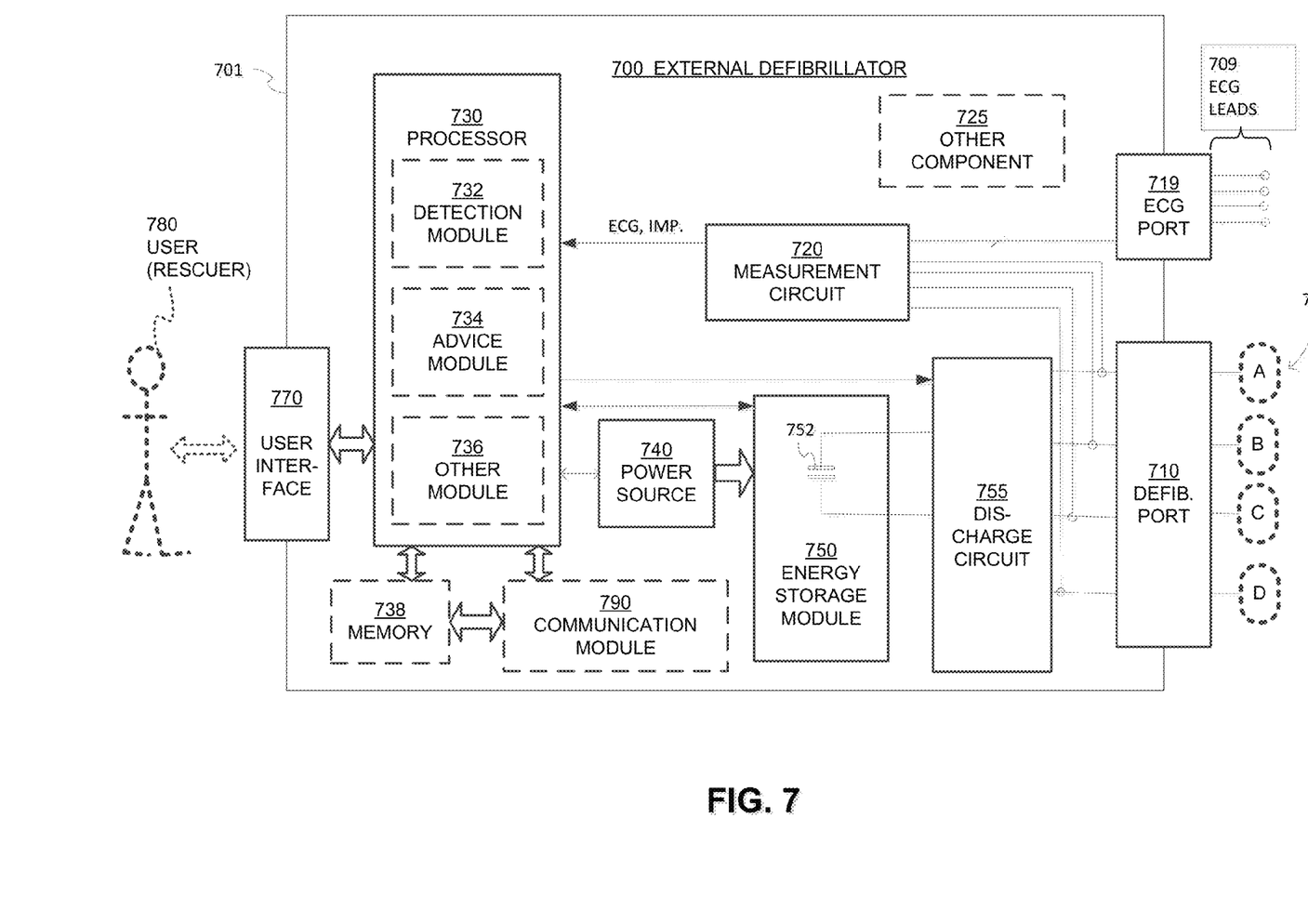
FIG. 7 is a diagram showing possible components of an external defibrillator made according to embodiments of the present invention.

FIG. 7 depicts a diagram showing possible components of an external defibrillator 700 made according to an embodiment of the present invention. These components can be, for example, in external defibrillator 500 of FIGS. 5A and 5B. In addition, these components of FIG. 7 can be provided in a housing 701, which is also known as casing 701.

External defibrillator 700 is intended for use by a user 780, who would be the rescuer. Defibrillator 700 typically includes a defibrillation port 710, such as a socket in housing 701. Defibrillation port 710 includes internal nodes (not shown). Defibrillation electrodes 704 (including electrode pads A-D), which can be similar to electrodes 504, 508, can be plugged in defibrillation port 710, so as to make electrical contact with the nodes. It is also possible that electrodes can be connected continuously to defibrillation port 710, etc. Either way, defibrillation port 710 can be used for guiding via electrodes to person 582 an electrical charge that has been stored in defibrillator 700 (i.e., in capacitor 752), as discussed below.

If defibrillator 700 is actually a defibrillator-monitor, then it will typically also have an ECG port 719 in housing 701, for plugging in ECG leads 709. ECG leads 709 can help sense an ECG signal, e.g. a 12-lead signal, or from a different number of leads. Moreover, a defibrillator-monitor could have additional ports (not shown), and another component 725 structured to filter the ECG signal, e.g., apply at least one filter to the signal so as to remove chest compression artifacts resulting from chest compressions being delivered to the person 582.

Defibrillator 700 may also include a measurement circuit 720. Measurement circuit 720 receives physiological signals from ECG port 719, and also from other ports, if provided. These physiological signals are sensed, and information about them is rendered by circuit 720 as data, or other signals, etc.

If defibrillator 700 is actually an AED, it may lack ECG port 719. Measurement circuit 720 can obtain physiological signals through the nodes within port 710 instead, when defibrillation electrodes 704 are attached to person 582 (FIG. 5). In these cases, a person's ECG signal can be sensed as a voltage difference between electrodes 704. Plus, impedance between electrodes 704 can be sensed for detecting, among other things, whether these electrodes have been inadvertently disconnected from the person.

Defibrillator 700 also includes a processor 730. Processor 730 may be implemented in any number of ways, for causing actions and operations to be performed. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 730 can be considered to have a number of modules. One such module can be a detection module 732, which senses outputs of measurement circuit 720. Detection module 732 can include a VF detector. Thus, the person's sensed ECG can be used to determine whether the person is experiencing VF.

Another such module in processor 730 can be an advice module 734, which arrives at advice based on outputs of detection module 732. Advice module 734 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 700 may further issue prompts for it, and so on. Processor 730 can include additional modules, such as module 736, for other functions. In addition, if other component 725 is indeed provided, it may be operated in part by processor 730, etc.

Defibrillator 700 optionally further includes a memory 738, which can work together with processor 730. Memory 738 may be implemented in any number of ways. Such ways include, by way of example and not of limitation, nonvolatile memories (NVM), read-only memories (ROM), random access memories (RAM), any combination of these, and so on. Memory 738, if provided, can include programs for processor 730, and so on. The programs can be operational for the inherent needs of processor 730, and can also include protocols and ways that decisions can be made by advice module 734. In addition, memory 738 can store prompts for user 780, etc. Moreover, memory 738 can store patient data.

Defibrillator 700 may also include a power source 740. To enable portability of defibrillator 700, power source 740 typically includes a battery. Such a battery is typically implemented as a battery pack, which can be rechargeable or not. Sometimes, a combination is used, of rechargeable and non-rechargeable battery packs. Other embodiments of power source 740 can include AC power override, for where AC power will be available, and so on. In some embodiments, power source 740 is controlled by processor 730.

Defibrillator 700 additionally includes an energy storage module 750. Module 750 is where electrical energy is stored, when preparing it for sudden discharge to administer a shock. Module 750 can be charged from power source 740 to the right amount of energy, as controlled by processor 730. In typical implementations, module 750 includes one or more capacitors 752, and so on.

Defibrillator 700 moreover includes a discharge circuit 755. Circuit 755 can be controlled to permit the energy stored in module 750 to be discharged to the nodes within defibrillation port 710, and thus also to defibrillation electrodes 704.

Circuit 755 can include one or more switches, half-bridges, or the like, as discussed above with reference to FIG. 2.

Defibrillator 700 further includes a user interface 770 for user 780. User interface 770 can be made in any number of ways. For example, interface 770 may include a screen, to display what is detected and measured, provide visual feedback to the rescuer for their resuscitation attempts, and so on. Interface 770 may also include a speaker, to issue voice prompts, etc. Interface 770 may additionally include various controls, such as pushbuttons, keyboards, and so on. In addition, discharge circuit 755 can be controlled by processor 730, or directly by user 780 via user interface 770, and so on.

Defibrillator 700 can optionally include other components. For example, a communication module 790 may be provided for communicating with other machines. Such communication can be performed wirelessly, or via wire, or by infrared communication, and so on. This way, data can be communicated, such as patient data, incident information, therapy attempted, CPR performance, and so on.

A feature of a defibrillator can be CPR-prompting. Prompts are issued to the user, visually or by sound, so that the user can administer CPR. Examples are taught in U.S. Pat. Nos. 6,334,070 and 6,356,785.

Conclusion

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

In general, the various features and processes described above may be used independently of one another, or may be combined in different ways. For example, this disclosure includes other combinations and sub-combinations equivalent to: extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations irrespective of other features in relation to which it is described. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example examples. The example systems and components described herein may be configured differently than described. For example, elements may be added to, removed from, or rearranged compared to the disclosed example examples.

Each of the processes, methods and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

It will also be appreciated that various items are illustrated as being stored in memory or on storage while being used, and that these items or portions of thereof may be transferred between memory and other storage devices for purposes of memory management and data integrity. Alternatively, in other embodiments some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), etc. Some or all of the modules, systems and data structures may also be stored (e.g., as software instructions or structured data) on a computer-readable medium, such as a hard disk, a memory, a network or a portable media article to be read by an appropriate drive or via an appropriate connection. Such computer program products may also take other forms in other embodiments. Accordingly, the present invention may be practiced with other computer system configurations.

While certain example or illustrative examples have been described, these examples have been presented by way of example only, and are not intended to limit the scope of the inventions disclosed herein. Indeed, the novel methods and systems described herein may be embodied in a variety of other forms. The accompanying claims and their equivalents are intended to cover such forms or modifications as would fall within the scope and spirit of certain of the inventions disclosed herein.

What is claimed:

1. A transthoracic defibrillator for external defibrillation, comprising:
    at least three electrodes configured to be attached to the thorax of a patient to establish at least two electrical paths across the thoracic cavity and through the heart of the patient, wherein each of the at least two electrical paths has an associated impedance; and
    a defibrillator circuit contained in a defibrillator housing, wherein the defibrillator circuit is operatively connected to the at least three electrodes and is configured to deliver a defibrillation waveform across each of the at least two electrical paths, and wherein the at least three electrodes are incorporated into a garment or belt that can be worn by the patient;

a measurement circuit configured to measure the impedance of each of the at least two electrical paths, wherein the measurement circuit is configured to measure impedance in at least one of the following ways: (a) simultaneously across at least two pairs of electrodes using carrier frequencies that differ by at least 5 kHz between each of the simultaneously tested pairs; and (b) sequentially between different pairs of electrodes;

wherein a parameter of the defibrillation waveform delivered along each electrical path is influenced by a measured impedance associated the electrical path; and wherein the at least two electrical paths form a first vector and a second vector, and the defibrillation waveforms comprise at least one of the following: (a) a sequence of non-zero voltages including a positive shock on the first vector, followed by a positive shock on the second vector, followed by a negative shock on the first vector, followed by a negative shock on the second vector; and (b) a sequence of non-zero voltages including a positive shock on the first vector, followed by a positive shock on the second vector, followed by a negative shock simultaneously on the first and second vectors.

2. The defibrillator of claim 1, wherein:
the measurement circuit is configured to determine the number of currently established electrical paths between the at least three electrodes; and
if only one electrical path is currently established, the defibrillator circuit has the capability to deliver the defibrillation waveforms across that only one currently established electrical path.

3. The defibrillator of claim 1, wherein:
the defibrillator circuit accepts input from a user to indicate which pairs of electrodes form designated electrical paths and which defibrillation waveforms are used on which designated electrical paths; and
the defibrillator circuit has the capability to deliver the indicated defibrillation waveforms across the designated electrical paths.

4. The defibrillator of claim 3, wherein there is only one designated vector; and the designated vector corresponds to the lowest measured impedance amongst all pairs of electrodes.

5. The defibrillator of claim 1, wherein:
the defibrillation circuit is configured to measure impedance at least once at a time that is after the defibrillator is put on the patient and before the patient is in cardiac arrest.

6. The defibrillator of claim 1, wherein the parameter is the energy delivered.

7. The defibrillator of claim 1, wherein the parameter is the waveform duration.

8. The defibrillator of claim 7, wherein the defibrillation circuit is configured to:
measure the impedance along one vector;
determine the pulse width of the defibrillation waveform across each vector based at least in part on the impedance measurement; and
cause the duration of the waveform along each vector to be substantially the same.

9. The defibrillator of claim 7, wherein the defibrillation circuit is configured to control the waveform duration along each vector to cause the energy delivered along each vector to be substantially the same.

10. The defibrillator of claim 1, wherein the parameter is the waveform tilt.

11. The defibrillator of claim 10, wherein the defibrillation circuit is configured to control the waveform duration along each vector to cause the waveform tilt along each vector to be substantially the same.

12. The defibrillator of claim 1, wherein a parameter of the defibrillation waveform along at least one vector is influenced by the measured impedance between the electrodes of a different vector.

13. The defibrillator of claim 1, wherein the defibrillator contains a single capacitor in an energy storage module; and the duration of the shock on each vector is determined by the impedance between the electrodes of that vector.

14. The defibrillator of claim 1, wherein the defibrillator circuit is configured to measure the patient's electrocardiogram via the electrodes also used to deliver the defibrillation waveforms.

15. The defibrillator of claim 14, wherein two of the at least three electrodes are configured to measure the electrocardiogram signal and a third of the at least three electrodes is configured as a reference electrode.

16. The defibrillator of claim 1, wherein:
the at least three electrodes include exactly four electrodes providing six possible electrical paths; and
a first set of vectors are two electrical paths chosen from the six possible electrical paths;
a second set of vectors are two electrical paths chosen from the six possible electrical paths, wherein the second set of vectors is different from the first set of vectors; and
if the first set of defibrillation waveforms delivered across the first set of vectors fail to establish a regular heart rhythm in the patient, the defibrillator circuit has the capability to deliver a second set of defibrillation waveforms across the second set of vectors.

17. A method of transthoracic defibrillation, comprising:
attaching at least two electrodes to the thorax of a patient to establish at least a first electrical path across the thoracic cavity and through the heart of the patient;
determining if the patient is in ventricular tachycardia (VT), ventricular fibrillation (VF), or atrial fibrillation (AF);
establishing at least a second electrical path if VF or AF is determined, wherein establishing at least a second electrical patent comprises attaching at least one additional electrode to the thorax of the patient to establish at least one additional electrical path across the thoracic cavity and through the heart of the patient; and
sending a defined amount of electrical energy as a first shock across at least one of the electrical paths.

18. The method of transthoracic defibrillation, comprising:
attaching two electrodes to the thorax of a patient to establish a first electrical path across the thoracic cavity and through the heart of the patient;
delivering a first shock to the patient;
determining if the first shock was effective in establishing regular heart rhythm;
if the first shock was not effective, attaching at least one more electrode to the patient;
delivering a multivector shock to the patient.

* * * * *